United States Patent [19]

Taumann

[11] 4,095,114
[45] June 13, 1978

[54] ARRANGEMENT FOR SCATTERING ELECTRONS

[75] Inventor: Leonhard Taumann, Lafayette, Calif.

[73] Assignee: Siemens Aktiengesellschaft, Berlin & Munich, Germany

[21] Appl. No.: 779,166

[22] Filed: Mar. 18, 1977

[51] Int. Cl.² ............................................. G21F 3/02
[52] U.S. Cl. .................................. 250/510; 250/514; 250/305
[58] Field of Search ............... 250/305, 526, 503, 510, 250/514

[56] References Cited

U.S. PATENT DOCUMENTS

| | | | |
|---|---|---|---|
| 2,724,059 | 11/1955 | Gale | 250/510 |
| 3,917,954 | 11/1975 | Boge | 250/510 |
| 4,006,361 | 2/1977 | Schriber | 250/510 |

*Primary Examiner*—Harold A. Dixon

*Attorney, Agent, or Firm*—Hill, Gross, Simpson, Van Santen, Steadman, Chiara & Simpson

[57] ABSTRACT

An arrangement is provided for scattering electrons in an electron accelerator capable of variable acceleration energies. The arrangement has two scattering foils arranged at a mutual spacing from one another along a direction of an electron beam. A first scattering foil in the beam direction has a constant thickness whereas a second scattering foil has a thickness which decreases from its center towards its margin. The first scattering foil comprises a set of foils each of which have a scattering capability which corresponds to a selectable acceleration energy. The appropriate member of the set is selected and placed in the beam as the first scattering foil so as to create a relatively constant intensity of radiation over a given volume. The second scattering foil, which is of a more costly and complex construction, remains unchanged in the electron beam.

11 Claims, 4 Drawing Figures

ARRANGEMENT FOR SCATTERING ELECTRONS

BACKGROUND OF THE INVENTION

1. Field of the Invention

The invention relates to an arrangement for scattering electrons, preferably in electron accelerators with variable acceleration energy, the arrangement comprising two mutually spaced scattering foils whereby the first scattering foil in the beam direction has a constant thickness and the second scattering foil has a thickness which decreases from the center to its margins.

2. Description of the Prior Art

In the case of electron accelerators which must expose several cubic decimeters of volume with a constant intensity, it is known in the art to use two different foils arranged at a distance from one another for scattering the electrons (see German Letters Pat. No. 9 599 37.).

According to the prior art, the first scattering foil in the beam direction serves for scattering the electron beam. The second scattering foil is to compensate or equalize the intensity of the scattered electron beam. Since the thickness of the first scattering foil may not be selected very large due to energy losses, and since the resulting homogeneity of the intensity distribution obtained in the beam cone scattered by the first foil is insufficient, the second scattering foil must have a thickness which decreases from its center towards its margin in order to have a greater reduction of the intensity in the center range than in the marginal range of the beam cone.

However, the scattering properties of such an arrangement are also dependent, in addition to the properties of the two scattering foils, on the mutual tuning of the two scattering foils; the centering of the second scattering foil with respect to the center beam; and the energy of the electrons which are to be scattered. Thus, a different arrangement is required for each acceleration energy. This is considered to be a large drawback since scattering foils, particularly the second one, are cumbersome to produce and thus expensive. Their exact centering with respect to the electron beam cone must, in addition, be very precise.

SUMMARY OF THE INVENTION

It is an object of this invention to provide a means whereby the electrons of an electron accelerator operating at variable acceleration energies can be scattered in an economically useful manner in order to be able to expose a greater volume with a constant intensity per volume element.

In accordance with the invention, if the acceleration energy is selected lower, an appropriate first scattering foil having decreased scattering properties can be placed into the beam path in order to adapt the overall scattering properties to the selected acceleration energy. The second scattering foil remains unchanged in the beam cone. In this manner it results that the second scattering foil, which is more expensive to produce and center, can be maintained in fixed position in the beam defining system without requiring a plurality of second scattering foils.

In an advantageous further development of the invention, the second scattering foil may be constructed of several concentric and rigidly superimposed circular disc-shaped foils of different diameters and thicknesses. It becomes possible in this manner to use foils which are readily available. This results in an important cost reduction.

An improvement of the scattering properties of the second scattering foil can be obtained when the margins of the individual circular disc-shaped foils are inclined in a further development of the invention.

DESCRIPTION OF THE PREFERRED EMBODIMENTS

Figure 1:
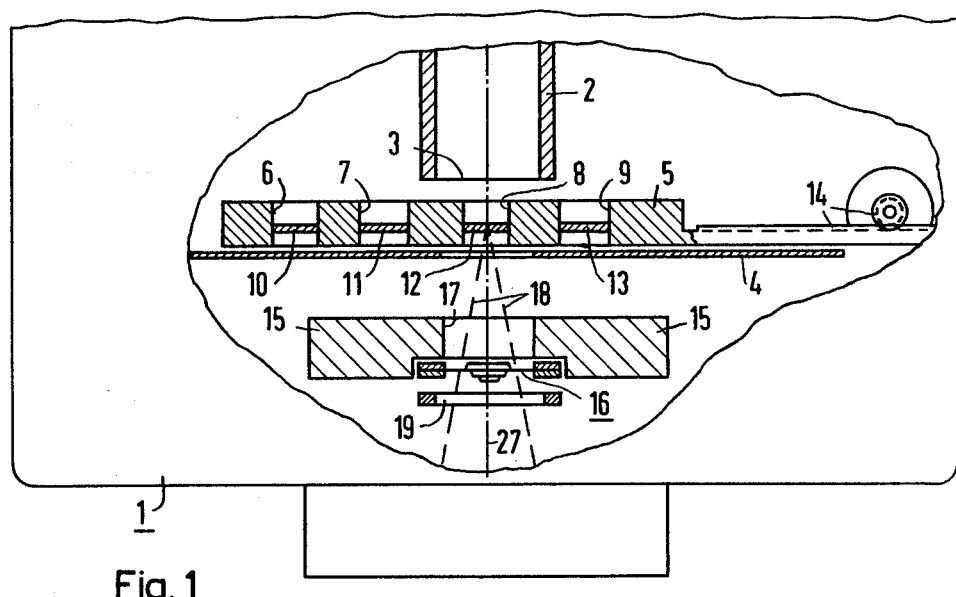
FIG. 1 is a representation of the arrangement of scattering foils of this invention in a beam defining system of an electron accelerator.

In the schematically illustrated beam defining system of an electron accelerator shown in FIG. 1, a portion of a vacuum tube 2 for the electron beam with an exit window 3 for electrons is shown. A sled 5 which can be longitudinally moved upon a carrier plate 4 is positioned behind the exit window 3 for the electrons in the beam direction. The sled 5 is provided with four borings 6, 7, 8, 9, arranged in one row. A scattering foil 10, 11, 12 or 13 of a given mass per unit area is placed into each boring. The foils consist of a material of as high an atomic weight as possible, preferably lead or tungsten. The sled 5 is associated with a motor-driven setting drive 14. Each of the scattering foils, by themselves, are of even thickness - (0.003 - 0.015 inch steel and 0.003 - 0.008 inch lead). The carrier 15 for the second scattering foil 16 is positioned behind the sled 5 in the beam direction. It has a passageway 17 for the scattered electron beam 18. The scattering foil 16, having mass per unit area which decreases from the center towards its margins, is inserted into the passageway 17 of the carrier 15. An ionization chamber 19 for measuring and supervising the beam exit is arranged behind the carrier 15 in the beam direction.

Figure 2:
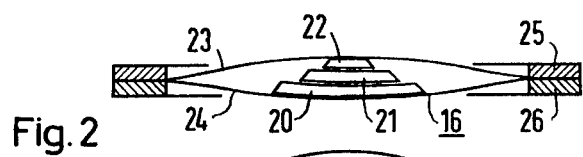
FIG. 2 is a cross-sectional view through a second scattering foil of this invention.
Figure 3:
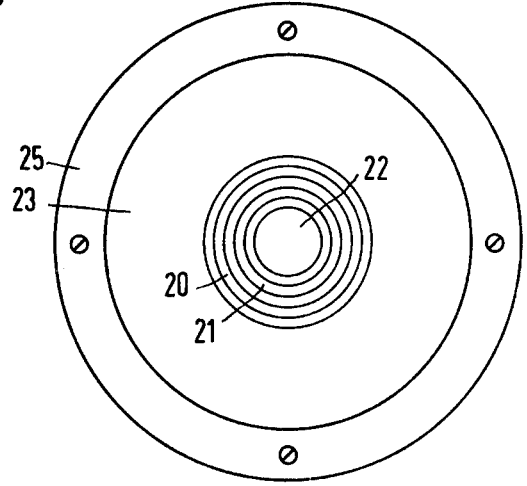
FIG. 3 is a plan view of the scattering foil of FIG. 2.

FIGS. 2 and 3 show the second scattering foils 16, of different mass per unit area, in an enlarged representation. The individual foils 20, 21, 22 have a different diameter and different thicknesses. They are superimposed or layered over one another in the manner of a pyramid. Their margins are inclined. They consist of a material of a low atomic weight such as aluminum which is preferred. However, it is also possible to use foils of an organic material. The foils 20, 21, 22 are held between two carrier foils 23, 24 which are constructed of organic material and made as thin as possible. These carrier foils are mounted between two rings 25, 26 arranged outside of the beam cone 18. The two rings are screwed against one another and against the carrier 15 for the second scattering foil 16.

Figure 4:
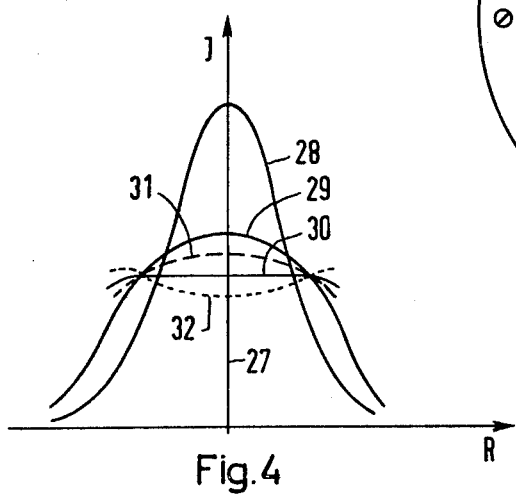
FIG. 4 illustrates on a graph the intensity distribution within the electron beam depending on the distance from the center beam and the effected scattering.

In FIG. 4, the relationship between the radiation intensity I and the distance R from the center beam 27 is illustrated as various curves on the graph. The curve 28 shows the intensity distribution impinging upon the first scattering foil. After this first scattering foil, the intensity maximum is clearly widened, as shown in curve 29. Due to the greater mass per unit area in the center of the second scattering foil, radiation is scattered and absorbed at the center portion of this beam cone to an increased extent.

The intensity decreases to a greater extent in the center portion due to the second scattering foil 16. Thus, the intensity distribution has the shape of curve 30 behind the second scattering foil 16. The dosage is completely compensated and equalized in the center portion of the beam cone 18. This portion of the beam cone can be utilized for the radiation exposure of a seat of disease, for example.

If, however, the acceleration energy of the electrons is reduced, they will be more strongly absorbed and scattered in the first scattering foil. The first scattering foil would produce a better compensated or equalized intensity path in front of the second scattering foil 16, as indicated by the broken curve 31 in FIG. 4. However, after a subsequent further scattering and absorption due to the second scattering foil, which has a greater absorption and scattering effect due to the reduced electron energy, the distribution would assume the undesired dotted path pf curve 32. In order to avoid this, the second scattering foil would have to be exchanged for one with a radially less decreasing mass per unit area. This requires a large number of expensive and mutually stacked scattering foils. These foils would have to be exchanged for each change of the acceleration energy. Such newly inserted scattering foils would have to be centered each time with respect to the centering beam which itself may not be aligned with respect to the axis of symmetry of the exit window 3.

In the case of the arrangement of the scattering foils in accordance with the invention, an adjusting mechanism 14 is switched on simultaneously with the switchover of the accelerator to another acceleration energy. The adjusting mechanism shifts the sled 5 with the scattering foils 10, 11, 12 or 13 until the boring 6, 7, 8 or 9 with the first scattering foils 10, 11, 12 or 13 for matching the selected acceleration energy is positioned directly ahead of the exit window 3 of the acceleration container. A special alignment with respect to the center beam is therefore not required since the first scattering foil is not shaped.

The so-called first scattering foils which are embedded in the sleds are thus associated with the acceleration energies, and can be selected at the electron accelerator in such a way that an appropriate first scattering foil having a decreased thickness or scattering capability, is shifted into the electron beam if the selected acceleration energy decreases. Thus, the intensity path for each acceleration energy directed at the second scattering foil 16 is brought to a value which in consideration of the scattering and absorption properties which are also changed for the second scattering foil 16 assumes the distribution curve denoted by 29 in FIG. 4. (This distribution being for an electron energy which is somewhat shifted for each acceleration energy, and which is thus shown only qualitatively here). The second scattering foil no longer needs to be exchanged. Since only a single second scattering foil is used, it can be centered during manufacture.

Although various minor modifications may be suggested by those versed in the art, it should be understood that it is intended to embody within the scope of the patent warranted hereon, all such embodiments as reasonably and properly come within the scope of this contribution to the art.

Claimed as my invention:

1. An arrangement for scattering electrons in an electron accelerator with selectable acceleration energies, comprising:
   (a) acceleration means for providing a beam of electrons;
   (b) first and second scattering foils arranged at a mutual spacing from one another along a direction of the beam for producing scattering properties;
   (c) the first scattering foil in the beam direction having a constant thickness;
   (d) the second scattering foil having a thickness decreasing from its center towards its margin;
   (e) means for adapting the scattering properties to the selected acceleration energy including a set of scattering foils, each having a scattering property corresponding to a selected acceleration energy, the scattering properties of the set of foils decreasing with decreasing acceleration energy, a corresponding one of said set of foils being placed by said means into the beam path of said first scattering foil for a second acceleration energy; and
   (f) said second scattering foil remaining unchanged in the beam.

2. An arrangement in accordance with claim 1, characterized in that the second scattering foil comprises several concentrically and rigidly superimposed circular disc-shaped foils of different diameters and thicknesses.

3. An arrangement in accordance with claim 2, characterized in that the margins of said disc-shaped foils are inclined.

4. An arrangement in accordance with claim 2, characterized in that the disc-shaped foils forming the second scattering foil are mounted between two carrier foils made of an organic material, said carrier foils being mounted between clamping rings.

5. An arrangement in accordance with claim 4 in which said organic material comprises polystyrol.

6. An arrangement in accordance with claim 1, characterized in that the first scattering foil is comprised of a material of high atomic number.

7. The arrangement of claim 6 in which said material of high atomic number consists of lead.

8. An arrangement in accordance with claim 1, characterized in that the second scattering foil is comprised of a material of a low atomic number.

9. The arrangement of claim 8 in which said material of low atomic number consists of aluminum.

10. An arrangement for scattering electrons in an electron accelerator with selectable acceleration energies, comprising:
   (a) acceleration means for providing a beam of electrons;
   (b) first and second scattering foils arranged at a mutual spacing from one another along a direction of the beam for scattering the electron beam to produce a relatively constant intensity of the beam over a given volume;
   (c) the first scattering foil in the beam direction having a relatively constant thickness;
   (d) the second scattering foil in the beam direction having a variable thickness;
   (e) said first scattering foil comprising one of a set of foils, each foil in the set having a differing scattering property which corresponds to a selected acceleration energy, the scattering properties of the set decreasing with decreasing acceleration energy; and
   (f) means for selecting a corresponding one of said set of foils and placing it in the beam in accordance with a selected acceleration energy.

11. The arrangement of claim 10 in which said means for selecting comprises a carrier with a sled movable thereover, said sled having mounted thereon the set of foils and being motor driven.

* * * * *